US00PP15247P3

(12) United States Plant Patent
Suzuki

(10) Patent No.: US PP15,247 P2
(45) Date of Patent: Oct. 19, 2004

(54) *KERRIA JAPONICA* PLANT NAMED 'FUBUKI NISHIKI'

(50) Latin Name: *Kerria japonica*
Varietal Denomination: Fubuki Nishiki

(75) Inventor: Yuji Suzuki, Kawaguchi (JP)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 10/027,597

(22) Filed: Dec. 19, 2001

(65) Prior Publication Data

US 2003/0115649 P1 Jun. 19, 2003

(51) Int. Cl.[7] ..... A01H 5/00

(52) U.S. Cl. ..... Plt./226

(58) Field of Search ..... Plt./226

*Primary Examiner*—Howard J. Locker

(74) *Attorney, Agent, or Firm*—Christie, Parker & Hale, LLP

(57) ABSTRACT

A new variety of *Kerria japonica* plant characterized by white flecked variegated foliage, yellow flowers with lighter yellow and greyed-green variegation, and slightly larger leaf size.

1 Drawing Sheet

Classification: The present invention relates to a new *Kerria japonica* (L.) DC [*Corchorus japonicus* Thunb.] plant.

Variety denomination: The new plant has the varietal denomination 'Fubuki Nishiki'.

BACKGROUND OF THE INVENTION

The present invention relates to a new and distinct variety of *Kerria japonica* (L.) DC [*Corchorus japonicus* Thunb.], which was discovered as a branch sport in a cultivated area of a controlled planting of *Kerria japonica* (unnamed, unpatented) in Kawaguchi City, Saitama Prefecture, Japan. The varietal denomination of the new variety is 'Fubuki Nishiki'.

The genus *Kerria* is included in the family Rosaceae, which comprises about 100 genera and 2,000 species of herbs, shrubs and trees native mostly to China and Japan. *Kerria* comprises one species, *Kerria japonica* (L.) DC, native to the temperate regions of eastern Asia, which possesses desirable ornamental characteristics.

*Kerria japonica* is a deciduous shrub with green leaves and glabrous branches. Leaves of the typical species are alternate, oval, long acuminate, serrated on the margins with pinnate venation. It generally has yellow flowers.

SUMMARY OF THE INVENTION

The new variety was discovered as a branch sport in a controlled planting of *Kerria japonica* (unnamed, not patented) and differs from its parent by white flecked variegated foliage, yellow flowers with lighter yellow and greyed-green variegation, and slightly larger leaf size. Asexual reproduction of the new variety by vegetative cuttings, performed in Lewisberry, Pa. and Vacaville, Calif. have confirmed that the distinctive characteristics of the new variety are stable and transmitted to succeeding generations, and the new variety reproduces true to type.

COMPARISON WITH PARENTS

'Fubuki Nishiki' is distinguished from its parent and all other varieties of *Kerria japonica* of which I am aware by its white flecked variegated foliage, yellow flowers with lighter yellow and greyed-green variegation and slightly larger leaf size. The parent plant has completely green foliage and solid yellow flowers.

BRIEF DESCRIPTION OF THE ILLUSTRATIONS

The accompanying illustrations show a specimen of the new cultivar in a photo illustration as true to color as is reasonably possible to make in an illustration of this character.

Figure 1:
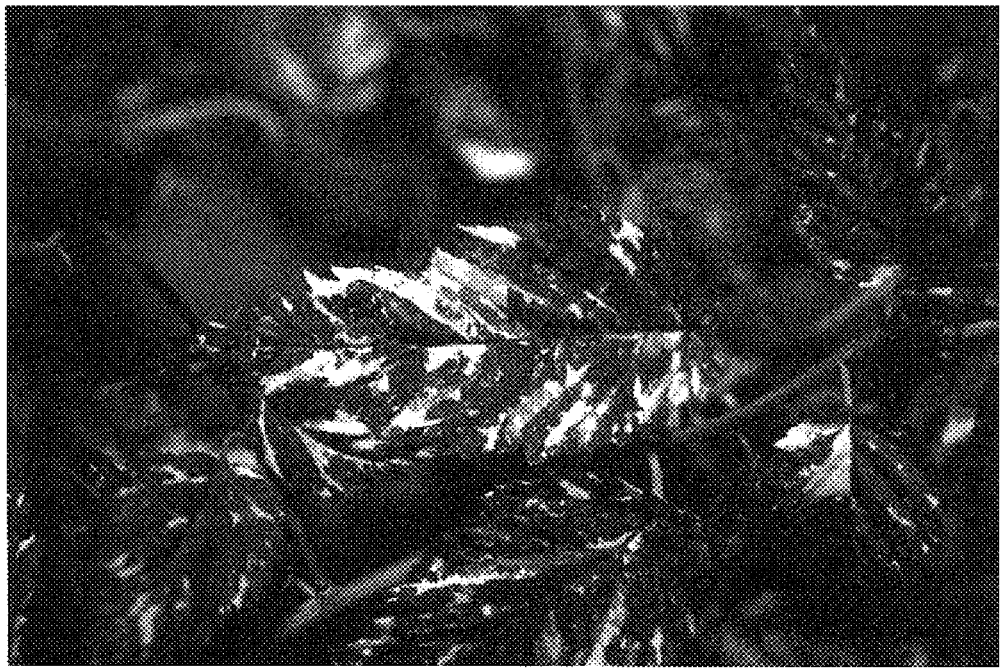
Figure 2:
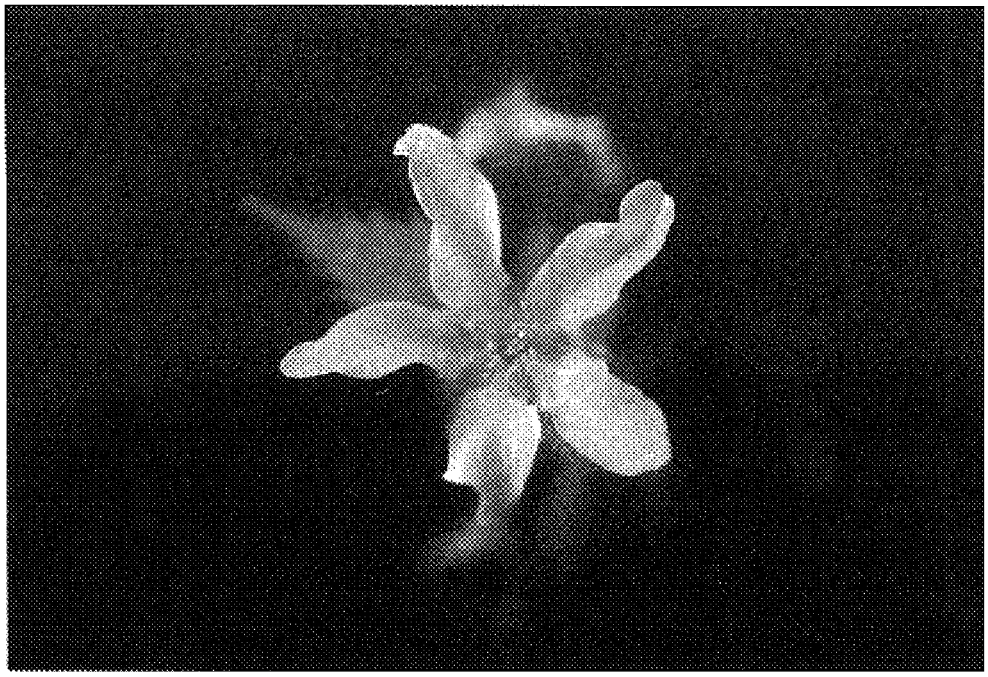

FIG. 1 illustrates the distinctive variegated foliage of 'Fubuki Nishiki'; and FIG. 2 illustrates the flower of 'Fubuki Nishiki'.

DETAILED DESCRIPTION OF THE INVENTION

'Fubuki Nishiki' has not been observed under all possible environmental, cultural and light conditions. The following observations, descriptions and color readings are of 3-year-old plants, in 5-gallon nursery containers, grown in Vacaville, Calif. and Lewisberry, Pa. In this description, color references are to The Royal Horticultural Society Colour Chart (1995) and terminology used in the color descriptions herein refers to plate numbers in this color chart. Phenotypic expression may vary with light intensity, cultural and environmental conditions.

CLASSIFICATION

Botanical: *Kerria japonica* (L.) DC. [*Corchorus japonicus* Thunb.].

Parentage: Branch sport of *Kerria japonica* (unnamed, not patented).

Propagation: Stem cuttings.

PLANT

Size: About 2 m tall and about 3 m across at 3 years of age; 1-year-old plants measured about 30 cm tall and about 25 cm across; and 2-year-old plants measured 125 cm tall and about 2 m across.

Habit: Upright; multi-branched shrub when young, with an increasingly spreading and pendulous habit in its second and third years of growth.

Branching:

*Lateral branches.*—Numerous, obliquely upright becoming pendant with age.

*Observed number branches.*—19.

*Size.*—Length: About 1 m long. Diameter: About 5 to 6 mm at base.

*Color.*—Near 139C. New Shoots: Near 139C.

LEAF

Shape: Ovate to oblong; leaf tip long; acuminate occasionally hooked; leaf base mostly cuneate to obtuse and occasionally cordate or truncate.

Size: About 5 to 10 cm long and 2.5 to 5 cm wide. (Parent plant has typical leaf size of 3 to 7 cm long and 2 to 3.5 cm wide.).

Arrangement: Alternate.

Margin: Coarsely and irregularly doubly serrate.

Texture/substance: Thin, chartaceous.

*Upper surface.*—Glabrous with impressed veins, nearly bullate.

*Under side.*—Glabrous to slightly pubescent with prominent veins.

VARIEGATION PATTERN

Flecked, splashed, and mottled in a random pattern. Areas of variegation are frequently long and narrow, parallel to the side veins of the leaf. There are additional smaller areas of variegation that show no consistent shape and are randomly distributed across the leaf. The variegation typically covers 25% to 50% of the leaf surface. Although the pattern of variegation is random, every leaf displays noticeable patterns of variegation. Foliage holds the initial variegation from emergence through the growing season.

Young Foliage:

*Green sections.*—Upper Side: Near 143A. Under Side: Near 143B.

*Variegated sections.*—Upper Side: Between 196C and 196D, and near 155B. Under Side: Near 196D.

Mature Foliage:

*Green sections.*—Upper Side: Near 143A. Under Side: Near 143B.

*Variegated sections.*—Upper Side: Between 196C and 196D, and near 155B. Under Side: Near 196D.

Venation pattern: Alternately pinnate depressed above, raised beneath.

Petiole:

*Size.*—Between about 0.5 to 1.5 cm.

*Coloration.*—Near 143A.

*Texture.*—Smooth.

*Internodes.*—Between about 1 to 8 cm.

Hardiness: USDA Zone 5 (20° F. to −10° F.).

Vigor: Rapid growth rate.

Pests/diseases: No pest or disease problems noted.

INFLORESCENCE

Bloom period:

*Outdoors.*—March to May.

*Greenhouse.*—Not observed in greenhouse conditions.

Flower: Rotate.

*Arrangement.*—Solitary, terminal on lateral branchlets.

*Size.*—About 3.5 cm wide.

Shape of inflorescence: Solitary, terminal on lateral branchlets.

Fragrance: None noted.

Lastingness of individual blooms: Between 3 to 5 days.

Flower petals:

*Typical number.*—About 5.

*Observed number.*—About 5.

*Shape.*—Ovate. Apex: Retuse occasionally apiculate. Base: Abruptly attenuate.

*Size.*—About 16 mm long; about 7 mm wide.

*Margin.*—Entire and smooth, often undulate.

*Curvature.*—Slightly inwardly cupped.

*Arrangement.*—Rotate.

*Color.*—Background color: Near 5B. Variegated section: Between 196C to 196D, with some areas of light yellow near 11B; along the margins and occasional random speckling elsewhere on the petal.

*Sepals.*—Shape: Pointed. Color — Background color: Near 194A. Variegation color: Near 155B.

REPRODUCTIVE ORGANS

Androecium:

*Stamens.*—Between about 30–40.

*Anther.*—Shape: Club shaped. Color: Near 11B.

*Pollen amount.*—Voluminous. Color: Near 11B.

Gynoecium:

*Pistil count.*—About 5. Length: About 2 mm.

*Stigma color.*—Near 11B.

*Style color.*—Near 11B.

*Ovary color.*—Near 11B.

Fruit type: Achene.

I claim:

1. A new variety of *Kerria japonica* plant substantially as shown and described.

* * * * *